US008354057B2

(12) United States Patent
Heselton et al.

(10) Patent No.: US 8,354,057 B2
(45) Date of Patent: Jan. 15, 2013

(54) APPARATUS AND METHOD FOR USING OZONE AS A DISINFECTANT

(76) Inventors: Doug Heselton, Surrey (CA); Nigel Boast, Kelowna (CA); Jim Hudson, Delta (CA); Gordon Esplin, North Vancouver (CA)

( * ) Notice: Subject to any disclaimer, the term of this patent is extended or adjusted under 35 U.S.C. 154(b) by 0 days.

(21) Appl. No.: 12/140,717

(22) Filed: Jun. 17, 2008

(65) Prior Publication Data

US 2008/0310992 A1  Dec. 18, 2008

Related U.S. Application Data

(63) Continuation-in-part of application No. 10/593,377, filed on Feb. 4, 2008, now abandoned, and a continuation of application No. 11/605,311, filed on Nov. 29, 2006, now abandoned.

(51) Int. Cl.
| | |
|---|---|
| A61L 9/00 | (2006.01) |
| A62B 7/08 | (2006.01) |
| A62D 3/00 | (2007.01) |
| C01B 13/10 | (2006.01) |
| B01L 1/04 | (2006.01) |

(52) U.S. Cl. .......... 422/28; 422/1; 422/29; 422/30; 422/33; 422/34; 422/121; 422/184.07; 422/184.04; 588/299; 588/249; 588/300; 588/301; 204/176; 454/187; 454/189; 43/124; 43/125; 43/129

(58) Field of Classification Search .......... 422/1, 28–30, 422/33–34, 121, 305, 186.04, 186.07; 588/299, 588/249, 300–301; 204/176; 454/187, 189; 43/124–125, 129

See application file for complete search history.

(56) References Cited

U.S. PATENT DOCUMENTS

| | | | |
|---|---|---|---|
| 5,368,816 | A | 11/1994 | Detzer et al. |
| 5,501,844 | A | 3/1996 | Kasting, Jr. et al. |
| 5,868,999 | A | 2/1999 | Karlson |
| 6,481,219 | B2 | 11/2002 | Palermo |
| 2002/0085950 | A1 | 7/2002 | Robitaille et al. |
| 2003/0127506 | A1 | 7/2003 | Braun, Jr. |
| 2003/0152480 | A1 | 8/2003 | Sham |
| 2004/0047776 | A1 | 3/2004 | Thomsen |
| 2004/0096354 | A1 | 5/2004 | Nomura et al. |
| 2004/0202570 | A1 | 10/2004 | Nadkarni et al. |
| 2004/0262241 | A1 | 12/2004 | Socha |
| 2005/0031486 | A1 * | 2/2005 | Mole et al. ............. 422/28 |
| 2008/0031770 | A1 | 2/2008 | Boast et al. |

(Continued)

FOREIGN PATENT DOCUMENTS

CA  2120628  4/1993

(Continued)

OTHER PUBLICATIONS

English Translation of JP 05148114.*

(Continued)

*Primary Examiner* — Jill Warden
*Assistant Examiner* — Monzer Chorbaji

(57) ABSTRACT

A method of sterilizing a closed environment is provided in which a disinfection apparatus is placed into the closed environment; it then generates ozone to a predetermined ozone concentration, following which the humidity of the closed environment is rapidly increased. A catalytic converter then reduces the ozone concentration to safe levels. When the ozone concentration is reduced to a predetermined safe level, the disinfection apparatus signals.

18 Claims, 7 Drawing Sheets

U.S. PATENT DOCUMENTS

2008/0213125 A1 9/2008 Heselton et al.

FOREIGN PATENT DOCUMENTS

| CA | 2311386 | | 6/1999 |
|---|---|---|---|
| CA | 2270512 | | 10/2000 |
| CA | 2459041 | | 4/2003 |
| CA | 2443046 | | 3/2005 |
| CA | 2443044 | | 4/2005 |
| DE | 3933620 | | 4/1991 |
| EP | 0 693 289 | | 1/1996 |
| EP | 1 500 404 | | 1/2005 |
| GB | 2273048 | | 6/1994 |
| JP | 05148114 | * | 6/1993 |
| JP | 2001286542 | | 10/2001 |
| WO | WO 01/72432 | | 10/2001 |
| WO | WO 03/089017 | | 10/2003 |
| WO | 03101498 | | 12/2003 |
| WO | WO 2005/087278 A1 | * | 9/2005 |
| WO | 2008014615 | | 2/2008 |

OTHER PUBLICATIONS

Ishizaki, et al.: "Inactivation of *Bacillus* spores by gaseous ozone" The Journal of Applied Bacteriology 1986 60(1), 67-72.

Mazaoka, et al.: "Ozone Decontamination of Bioclean Rooms" Applied Environmental Microbiol. 1982 43(2), 509-513.

Elford, et al.: "An investigation of the merits of ozone as aerial disinfectant" Journal of Hygiene 1942, 42, 240-265.

Shin, et al.: "Reduction of Norwalk virus, Poliovirus 1, and Bacteriophage MS2 by ozone disinfection of water" Applied Environmental Microbiol. Jul. 2003, 69(7), 3975-3978.

Keswick, et al.: "Inactivation of Norwalk virus in drinking water by chlorine" Applied Environmental Microbiol. Aug. 1985, 50(2), 261-264.

Vaughn, et al.: "Inactivation of human and simian rotaviruses by ozone" Applied Environmental Microbiol, Sep. 1, 1987, 53(9), 2218-2221.

Sato, et al.: "Virucidal effect of ozone treatment of laboratory animal viruses" Jikken Dobutsu, Experimental Animals Apr. 1990, 39(2), 223-229.

Bolton, et al.: "Biological effects of ozone aerosol on five groups of animal viruses" Abstract of the annual meeting of the . . . Meeting 1980 vol. 167, p. 208 Q89.

Suphachai, et al.: "Capsid functions of inactivated human picornaviruses and feline calicivirus" Applied Environmental Microbiol. Jan. 2003, 69(1), 350-357.

Suphachai, et al.: "Ultraviolet inactivation of feline calicivirus, human entercivruses and coliphages" Photochemistry & Photobiology 2002 76(4), 406-410.

Doultree, et al.: "Inactivation of feline calicivirus, a norwalk virus surrogate" J. Hosp. Infect. Jan. 1999 41(1), 51-57.

International Search Report of PCT/CA2005/000412 (filed Mar. 18, 2005) mailed Jul. 6, 2005.

Written Opinion of the International Searching Authority of PCT/CA2005/000412 (filed Mar. 18, 2005) mailed Jul. 6, 2005.

"Owner's Manual—Models RA 3500 and RA 3500-2"; Treated Air Systems Mfg. Inc.; Surrey, Canada; published 2003 or earlier.

International Search Report for PCT/CA2007/001361 (WO2008/014615) dated Nov. 23, 2007.

International Preliminary Report on Patentability for PCT/CA2007/001361 (WO2008/014615) dated Dec. 8, 2008.

Supplementary European Search Report for EPO application 05730090 (EP1755689) dated Feb. 28, 2008.

Supplementary European Search Report for EPO application 07785025 (EP2051743) dated Sep. 23, 2009.

Search Opinion for EP2051743 dated Sep. 23, 2009.

* cited by examiner

US 8,354,057 B2

APPARATUS AND METHOD FOR USING OZONE AS A DISINFECTANT

This application is a continuation in part of U.S. patent application Ser. No. 10/593,377 and a continuation of Ser. No. 11/605,311, which are hereby incorporated by reference, and claims the benefit of U.S. Provisional Patent No. 60/553,937 filed Mar. 18, 2004; No. 60/625,101 filed Nov. 5, 2004; No. 60/656,888 filed Mar. 1, 2005; No. 60/834,794 filed Aug. 2, 2006; No. 60/843,762 filed Sep. 12, 2006; and No. 60/847,920 filed Sep. 29, 2006.

FIELD OF THE INVENTION

This invention relates to tools and methods for disinfecting closed environments, and more particularly to the use of ozone to disinfect a closed environment, such as a room.

BACKGROUND OF THE INVENTION

People traveling around the world have resulted in the rapid spread of emerging viruses and other diseases. If a disease becomes prevalent in a particular city, it can quickly spread internationally due to travel of the originating city's inhabitants. Once the disease is identified and infected individuals isolated, the disease has often already spread to high-density municipal areas, potentially in other countries, where it can be very difficult to control.

An example of such a disease is found in the rapid spread of Severe Acute Respiratory Syndrome (SARS), which has a high mortality rate and can be difficult to treat. It is also very difficult to screen infected people and prevent them from spreading the disease. In particular, the spread of such diseases poses a high risk to the hospitality industry, and can lead to reduced earnings and share prices of public companies in the hospitality sector. The aggressive spread of SARS from Asia to other countries including the United States and Canada has challenged the airline, hospitality and tourism industries as well as hospitals. The spread of SARS also had a negative impact on affected countries' economies, including that of major cities such as Toronto.

SARS is not the only virus of concern. A variety of airborne, gastro enteric and enteric viruses, including varicella zoster (chicken pox), measles virus, rhinovirus (cold), influenza virus (flu), poliovirus, rotavirus, hepatitis A, norovirus, adenovirus, and emerging viruses all represent risks of contagion and infection. The spread of bacterial infections and fungus can also be of significant concern, particularly when drug-resistant varieties of bacteria occur.

Such diseases are also of concern in the health care sector. For example, *clostridium difficile* (a human pathogenic bacterium of the intestine) is very difficult to remove when infected individuals are kept at a hospital. Health care workers and future patients may be put at risk in such situations.

Ozone has long been recognized as an effective biocide (a biochemical disinfectant) in aqueous form, and is also a powerful deodorizer in a gaseous form, having a number of attractive features. For example, gaseous ozone is pervasive in a closed space. Ozone is also highly effective as a viricide, and is inexpensive to administer, as ozone generators are plentiful and easy to install and operate.

Ozone is naturally formed, particularly in the upper atmosphere, when high-energy ultraviolet rays sever conventional oxygen ($O_2$) bonds, creating free radical oxygen atoms, which then react with other $O_2$ molecules to form ozone ($O_3$). Ozone is also formed naturally such as during lightning storms, at ocean beaches, and waterfalls.

The structure of ozone is highly reactive, and consequently ozone has a short half-life (about 30 minutes). When ozone breaks down, it produces oxygen and a free radical oxygen atom. This oxygen free radical is a powerful oxidant.

There are several ozone generators described in the prior art. For example, U.S. Pat. No. 5,904,901 to Shimono discloses a deodorization/odor-removal/disinfection method and deodorization/odor-removal/disinfection apparatus.

Prior art relating to the sterilization of hotel rooms and the like using ozone includes JP4038957A2, which discloses a determination of the time a room should be exposed to a particular concentration of ozone. JP2237565A2 discloses an indoor sterilizing method, which includes placing an ozone generator in a room, generating a level of ozone, leaving the ozone at that level for a period of time, and then decomposing the ozone.

Another prior art ozone generator is disclosed in US Patent Application Pub. No. 2005/0031486 to Mole et al., entitled "Sterilization and Decontamination". Mole et al. discloses an ozone generator that generates ozone after the humidity in the environment has reached at least 75%. The ozone generator then raises the ozone level to 10 ppm, allows a certain amount of time to pass, and then releases hydrocarbons to a concentration up to 20 ppm until the ozone level is depleted.

What is missing in the prior art is a timely way of delivering ozone to a closed environment, using other factors to minimize the time necessary for the ozone to carry out its purpose, and efficiently removing the ozone from the environment.

SUMMARY OF THE INVENTION

A method of disinfecting a closed environment is provided, including (a) generating gaseous ozone into the closed environment to a predetermined ozone concentration; (b) after reaching the predetermined zone concentration, rapidly increasing the humidity of the closed environment to a predetermined relative humidity level of greater than 80%; (c) after reaching the predetermined humidity level, depleting the ozone; and (d) when the ozone concentration is reduced to a predetermined safe level, signalling.

The predetermined ozone concentration may be within 15 to 40 ppm, or 20 to 30 ppm. The ozone may be depleted using a catalytic converter and passing ozonated air through a manganese dioxide tray and an activated carbon tray.

The humidity of the closed environment may be raised to a level of greater than 90% by an ultrasonic humidifier. The closed environment may be restricted, and the signalling may be via turning on a LED or turning off a sound.

A disinfection apparatus is provided including a timer; an ozone generator; a catalytic converter having a manganese dioxide tray and an activated carbon tray; a plurality of wheels; a sound generator; an ozone sensor; and a first fan to draw ozonated air into the catalytic converter. The disinfection apparatus may include an ultrasonic humidifier. The sound generator may generate an unpleasant sound when the ozone sensor senses an ozone level above a predetermined safe ozone level.

DETAILED DESCRIPTION OF THE INVENTION

Figure 1:
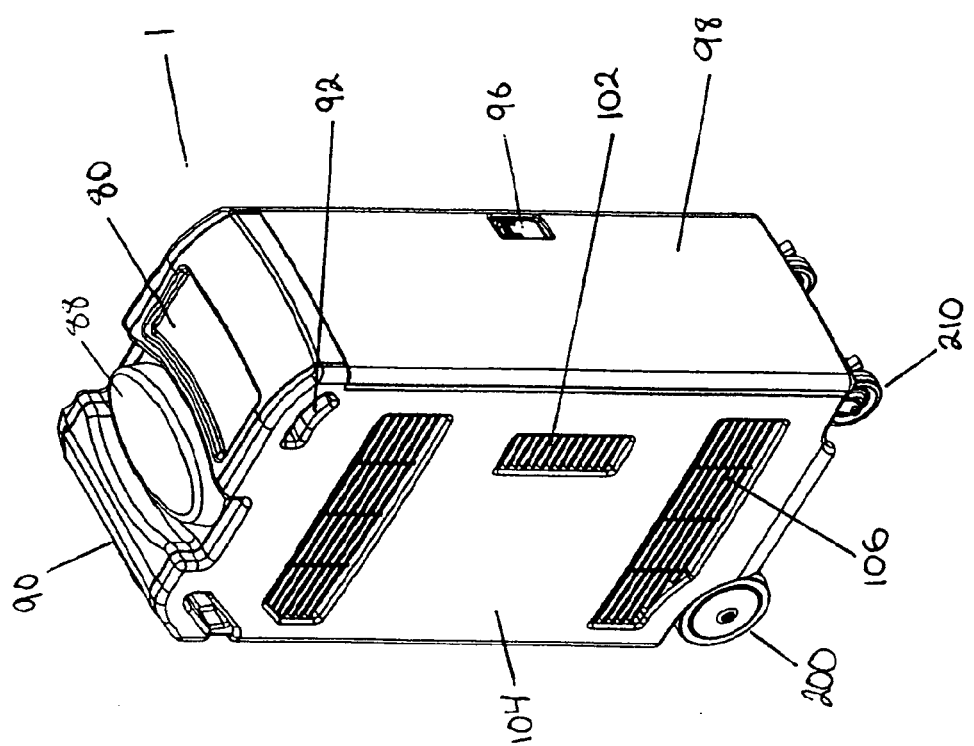
FIG. 1 is a perspective view of a disinfection apparatus according to the invention.

Unless otherwise stated references to ozone in this document refer to ozone in a gaseous state.

A difficulty with using ozone as a disinfectant is that the concentrations and exposure times required for ozone to be an effective disinfectant are considered to be toxic for humans. Such concentrations and exposure times may also generate noxious by-products from chemical reactions with fabrics commonly found indoors (particularly in carpets). For example, ozone may react with chemicals in carpets to create formic acid. Exposure to elevated ozone concentrations may irritate the lungs and have other side effects, including throat irritation, shortness of breath and coughing. Consequently several agencies have discouraged the use of ozone to sanitize indoor spaces and have set maximum safe levels of ozone to be from 0.05 parts per million ("ppm") to 0.10 ppm for an eight hour exposure.

Ozone is effective against many types of organisms, including retroviruses, both enveloped and naked viruses, bacteria and fungus. Specific diseases which ozone has been shown to be effective against include: MS2 Coliphage; Poliovirus Type 1 and Type 3; Hepatitis A; Enteroviruses; Rotaviruses; HIV; SA11 and enteric viruses; Influenza viruses; noroviruses and Rhinoviruses. Ozone may also be used to kill SARS viruses, infectious prions, and bacteria, and can also disinfect foodstuffs and sterilize medical equipment.

The level of ozone concentration required to be effective and achieve over 95% (and often over 99%) mortality rates of viruses and other disease causing agents varies depending on the time the agents are exposed to the ozone. One constant is that the ozone concentration necessary is preferably well above the safe levels for human exposure and therefore precautions should be taken to prevent such exposure. Ozone concentrations of approximately 100 ppm are extremely effective to kill infectious agents and may require exposure times for as little as five (5) minutes. Lower ozone concentrations (for example as low as 15 ppm) are also effective, although, in the case of such lower quantities of ozone, it may take more time (such as 20 to 30 minutes) for the ozone to be effective.

The Process of Using Ozone as a Disinfectant.

The present invention includes portable equipment, specifications and operating procedures to provide adequate ozone exposure in enclosed indoor spaces to achieve an effective degree of disinfection followed by rapid removal of the ozone and attendant gaseous by-products produced by the reaction of ozone with carpet and furniture fabrics.

The invention may include identifying the variables impacting the safe and effective use of ozone as a disinfectant in the hospitality and other industries. In summary, the invention provides for:

1. Rapid elevation of ozone levels to 20-25 ppm within a closed interior environment, combined with airflow to spread the gaseous ozone within the closed environment (this step normally takes about 15 minutes);

2. After reaching the desired ozone level, rapidly raising the humidity of the closed environment until reaching a humidity level of 80% or more (this step normally takes about 4-8 minutes); and 3. Rapid consumption of ozone using a catalytic converter to reduce the ozone concentration to levels safe for human exposure (this step normally takes about 15 minutes).

Figure 6:
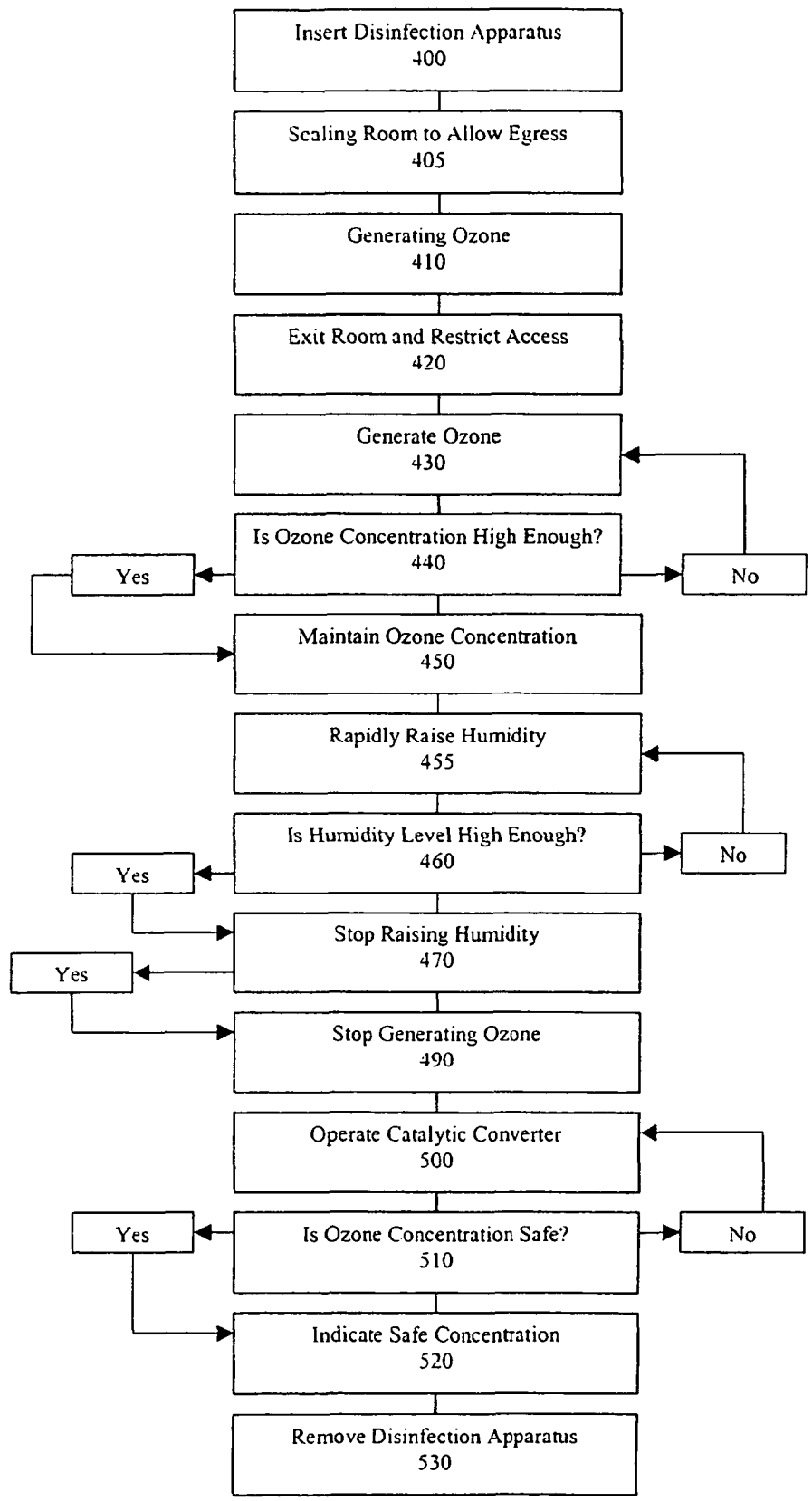
FIG. 6 is a flow chart showing the use of an disinfection apparatus according to the invention.

In a preferred embodiment the above steps should take about 15 to 40 minutes to disinfect a typical hotel room or cruise ship cabin. As an example, as seen in FIG. 6, a preferred method according to the invention may include the following steps:

a) inserting a portable disinfection apparatus in a closed interior environment, such as a hotel room or cruise ship cabin (step 400);

b) elevating the ozone concentration in the closed environment to a level sufficient to act as a disinfectant and viricide (typically 20-25 ppm) taking into account the size, temperature and airflow of the closed environment (step 410) and using a plurality of fans within the disinfection apparatus to spread the gaseous ozone throughout the closed environment;

c) restricting access to the closed environment while the ozone levels are elevated to prevent human exposure while the ozone concentration is dangerously high (step 420);

d) rapidly increasing the humidity of the closed environment to a level of 80% or more (step 455);

e) consuming the ozone and any gaseous aldehyde by-products by using a catalytic converter for a period of time, until the ozone concentration is below toxic levels (step 500); and f) removing the portable disinfection apparatus from the closed environment (step 530).

In further detail, with reference to FIG. 6, the process begins with the insertion of the disinfection apparatus into a closed environment (step 400). Examples of appropriate environments include hotel rooms, cruise ship cabins, hospital rooms, dormitory rooms, airplane cabins, long term care facilities, prisons, and larger public spaces (which may require multiple disinfection apparatuses). The room is preferably easily closed to public access (step 405) so that employees or guests will not be exposed to high concentrations of ozone. Examples of closing such an environment to public access include simply locking the door of a hotel room or cruise ship cabin when it is not in use by a guest, or posting signs and blocking access to the closed environment. In a preferred embodiment, magnetic flaps may be used to seal doors, etc. Any windows in the closed environment should be closed and any ventilation systems turned off (although fans unconnected to a ventilation system may remain on). Note that as the user of the ozone generator is still inside the room, it is important that it not be difficult to exit the closed environment quickly.

The user will then preferably turn on the ozone generator to being generating ozone (step 410) and exit the closed environment and restrict access (step 420). Preferably the ozone generator has a timer such that when it is turned on, there is a period of time (for example one or two minutes) before the ozone generator will begin generating ozone. This provides time for the user to exit the closed environment without exposure to the ozone.

In some embodiments of the invention, the user will have to adjust the ozone generator so that it will produce the appropriate amount of ozone within the appropriate time based on humidity, temperature variations, air flow and the like. It may also be necessary for the user to enter information about the room size (for example a menu of options such as "Suite", "Single" or "Double" could be displayed from which the appropriate selection is made). Alternatively, in a preferred embodiment, the disinfection apparatus will have sensors to measure these indicia, such as ozone level, temperature and humidity, and the disinfection apparatus will have a processor on a circuit board to automatically calculate the appropriate concentration of ozone that should be achieved, and be able to run diagnostic tests.

The access restriction to the closed environment (step 420) should be maintained while the ozone concentration is elevated, to prevent exposure to the ozone. The closed environment does not need to be airtight, for example closing the doors and windows of a hotel room is sufficient. Fans within the closed environment should be turned on (unless they are connected to ventilation systems). The entrance to the closed environment should be locked and/or a sign or warning light used to indicate that entry should not be permitted during the period when ozone concentrations are elevated.

The ozone generator then generates ozone (step 430) until the appropriate concentration is reached (step 440). Examples of sufficient ozone concentrations in a typical hotel room or cruise ship cabin would be 20 to 25 ppm. After the ozone concentration has reached the desired level, preferably as detected by the ozone sensor, the ozone generator generates only enough ozone to maintain the preferred ozone concentration (step 450). In alternative embodiments of the invention, the ozone generation may cease as this time. If, after a specified time period, for example 15 minutes in a small hotel room, the desired ozone level is not reached, then the disinfection apparatus will stop generating ozone, and proceed through the rest of the process, but provide a warning to the user that the desired ozone level was not reached.

The humidity level within the closed environment should then be raised rapidly to a predetermined level, preferably a level of 80% or more, such as 90% (step 455). The humidifier may be within the body of the disinfection apparatus, or may be a separate device. In a preferred embodiment, the humidifier is an ultrasonic humidifier and raises the humidity of the closed environment to 80 or 90% within 4 or 5 minutes. Once the desired humidity level is raised to the predetermined level (step 460), the humidifier is turned off (step 470), as is the ozone generator (step 490).

The ozone then begins to dissipate, both naturally, and preferably by the use of an appropriate catalyst (step 500). The ozone concentration is preferably measured (step 510) as the ozone is dissipated (as may be gaseous aldehyde by-products) for a period of time taking into account the ozone levels, the humidity (which is also decreasing), the temperature, the airflow and the size of the closed environment, until the ozone concentration is below toxic levels at which point the disinfection apparatus signals the closed environment is safe to enter using an LED, a noise (or cessation of a warning noise), a wireless transmission to a PDA, or the like (step 520).

In a preferred embodiment the catalytic converter is housed within the disinfection apparatus and uses a manganese dioxide catalyst. The catalytic converter preferably includes two trays, a manganese dioxide tray, and an activated carbon tray, and a fan to draw the ozonated air from the closed environment into the catalytic converter. The activated carbon assists in removing ozone at low levels and also removes the aldehyde by-products.

Once the appropriate amount of time has passed and the ozone sensor has indicated the ozone concentration is sufficiently low, the disinfection apparatus is removed from the closed environment and can be used in a different closed environment (step 530).

The Disinfection Apparatus

Figure 2:
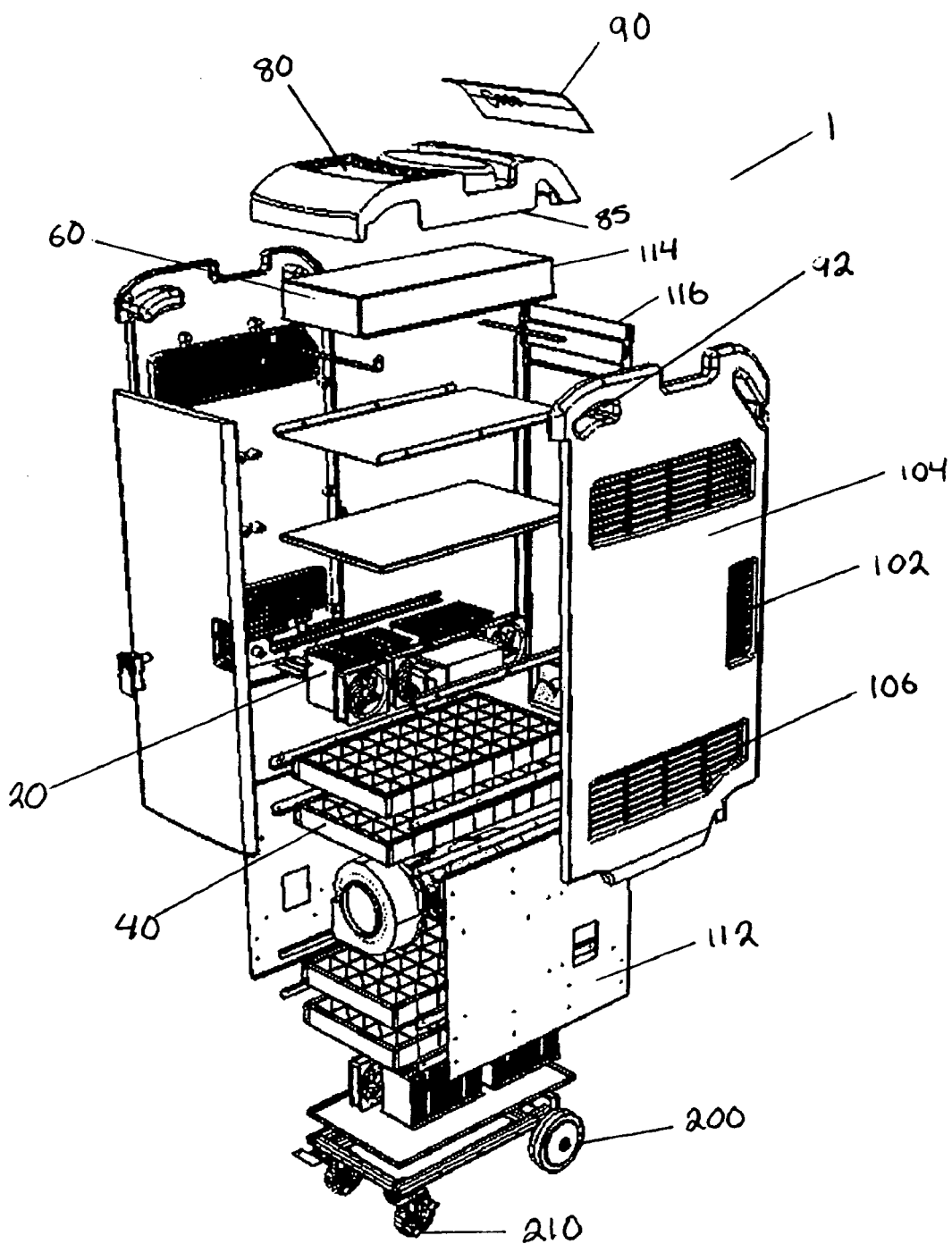
FIG. 2 is an exploded view thereof, showing the interior components of the disinfection apparatus.

The previously described method can be used with a variety of disinfection apparatuses, however an embodiment of a preferred disinfection apparatus is shown in FIGS. 1 and 2. The disinfection apparatus, generally indicated as 1, preferably generates gaseous ozone using an ozone generator 20. Ozone generator 20 uses corona discharge or ultra violet light or other ozone generation means as known in the art. The corona discharge process creates ozone using air in the closed environment that passes through disinfection apparatus 1 by using a multiplicity of fans (not shown), or alternatively air can be introduced into the closed space from disinfection apparatus, for example medical oxygen as such air is ozonated. The disinfection apparatus preferably also has an ozone depletion means such as an ozone scrubber or catalytic converter 40. The disinfection apparatus shown in FIGS. 1 and 2 is meant to be used with a detached humidifier, although alternative embodiments of the disinfection apparatus include a humidifier. Also disinfection apparatus 1 preferably has sensors, particularly an ozone sensor 60 for determining the concentration of ozone in the closed environment.

Disinfection apparatus 1 also includes a plurality of features for ease of use. Tray 80 is positioned within top panel 85 and allows users to store miscellaneous items. Extending member 88 is present to allow an electric cord to wrap around member 88 when disinfection apparatus 1 is not in use. Control panel 90 includes various means for controlling disinfection apparatus 1, including timers, on/off switches, and the like, and also includes displays of information, such as ozone levels, temperature and relative humidity. Control panel 90 is used to communicate with electronic components 114, including ozone sensor 60. Insets 92 on either side of disinfection apparatus 1 allow for easy lifting of disinfection apparatus for storage on pallets and the like. Handle 96 is present for ease of opening front panel 98.

Exhaust vents 102 are present in side panels 104 to exhaust cleaned air from disinfection apparatus 1 after passing through catalytic converter 40. Ozone exhaust vent 106 allows the ozone generated to exit disinfection apparatus 1 into the closed environment. Side panels 104, back panel 116 and frame 112 are used to support the interior components of disinfection apparatus 1.

Figure 3:
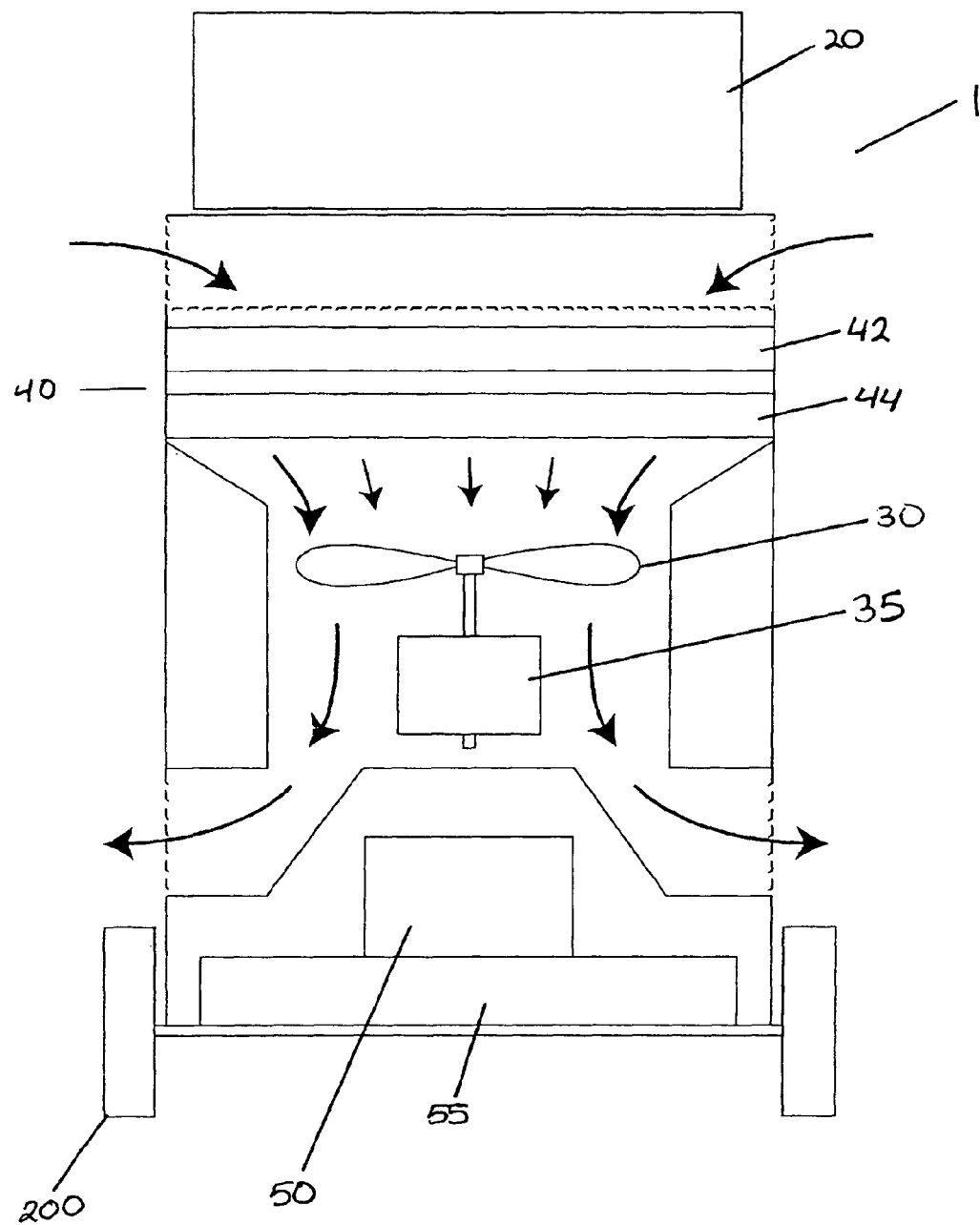
FIG. 3 is a front cross sectional view of an alternative embodiment of a disinfection apparatus according to the invention.
Figure 5:
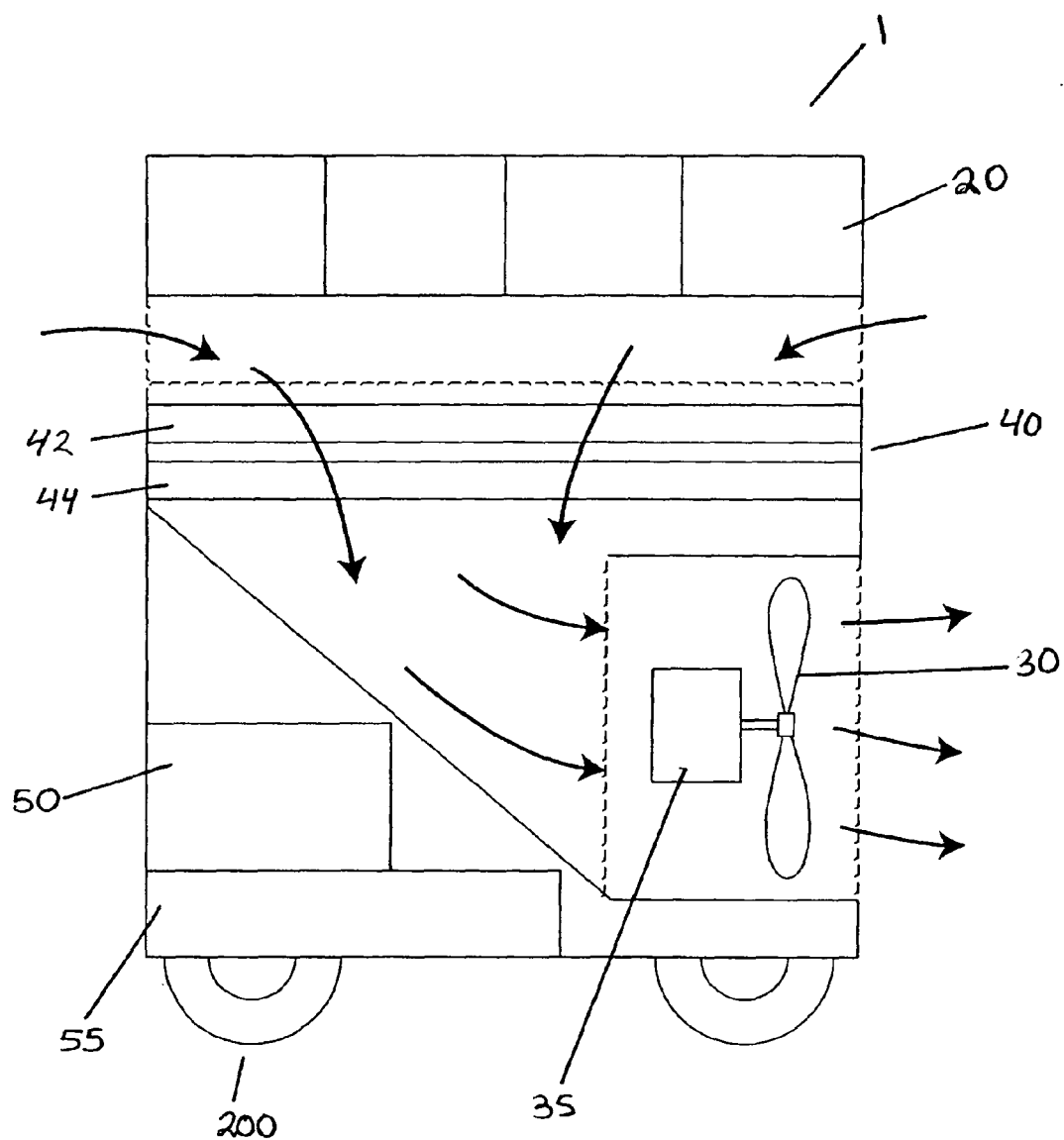
FIG. 5 is a side view thereof of an embodiment of the catalytic converter within a disinfection apparatus according to the invention.

Catalytic converter 40 is shown in detail in FIGS. 3 and 5, which represent alternative embodiments of disinfection apparatus 1. The key difference in these embodiments is that humidifier 50 is within disinfection apparatus 1, whereas in the previous embodiment, the humidifier is exterior to disinfection apparatus. Note the embodiments of disinfection apparatus 1 shown in FIG. 3 is different from that of FIG. 5 in the placement of fan 30 and motor 35 and the resultant air flow. Catalytic converter 40 allows disinfection apparatus 1 to quickly deplete the concentration of ozone to levels acceptable for humans. Catalytic converter 40 preferably uses manganese dioxide tray 42 and activated carbon tray 44. Fan 30 draws the ozonated air from outside of disinfection apparatus 1 through manganese dioxide tray 42 and activated carbon tray 44 as shown by the arrows in FIGS. 3 and 5. Catalytic converter 40 also depletes the ozonated air of aldehyde, nitroxides and any other noxious gases generated as by-products of the ozone reacting with articles in the environment, such as carpets, by the action of activated carbon tray 44. Another factor in the depletion of the ozone is the natural half-life of ozone, which is about 25 to 30 minutes.

Humidifier 50, whether internal or external to disinfection apparatus 1, is used to modify the relative humidity of the air volume after the desired ozone level has been reached. Accordingly, humidifier 50 is used after the ozone generation process, to raise the relative humidity of the closed environment to 80% or more. After reaching the desired level of humidity, (e.g. 80 or 90% or even greater) the humidifier should cease operating. Humidifier 50 is preferably an ultrasonic humidifier to allow the rapid increase in humidity to take as little as 4 or 5 minutes. As seen in FIGS. 3 and 5, water storage 55 is available within disinfection apparatus 1 to allow for rapid humidification of the closed environment. Fans (not shown) will assist in the operation of humidifier 50.

Disinfection apparatus 1 should either be sufficiently small and light enough to be easily carried or should be mounted on a trolley or affixed with other movement means, such as wheels 200 and/or castors 210, which, as shown in FIG. 1, may be mounted on the rear and front of disinfection apparatus 1, respectively. Alternatively disinfection apparatus 1 could be a fixture within the closed environment. In a preferred embodiment disinfection apparatus 1 is affixed with wheels and/or castors so that it can easily be moved from room to room within a larger structure (such as a hotel, a residence, a hospital or a cruise ship). In an alternative embodiment, disinfection apparatus 1 may have only two wheels, and may be moved by a user via handles or the like.

Disinfection apparatus 1 also preferably has ozone sensor 60 to detect the ozone levels within the closed environment. This is so that users can determine when the ozone concentration is low enough to allow safe entry into a room. In a preferred embodiment of the invention, disinfection apparatus 1 will indicate that the ozone concentration is safe and transmit a signal using transmitter 80 to a device (a mobile phone, PDA or the like) indicating that the environment is now safe to enter. Alternatively the signal can be transmitted to control panel 90, which will manipulate a LED on the outside of the room (e.g. red for high concentrations, and green for lower safe concentrations). Preferably more than one ozone sensor will be present in the closed environment (in different locations within the environment) to ensure ozone levels have dropped sufficiently (each remote ozone sensor will transmit the local ozone level to disinfection apparatus 1). In an alternative embodiment, disinfection apparatus 1 will create an unpleasant high-pitched noise when ozone levels are at an unsafe level, to warn users, and will cease the noise when safe ozone levels are reached.

In the case of a power interruption, disinfection apparatus 1 will default to catalytic converter 40 rather than try to continue with ozone generation (i.e. disinfection apparatus 1 defaults to a safety position). Also, in a preferred embodiment, disinfection apparatus 1 has a battery, instead of an electrical cord (not shown) so that it is independent of external power sources.

Figure 4:
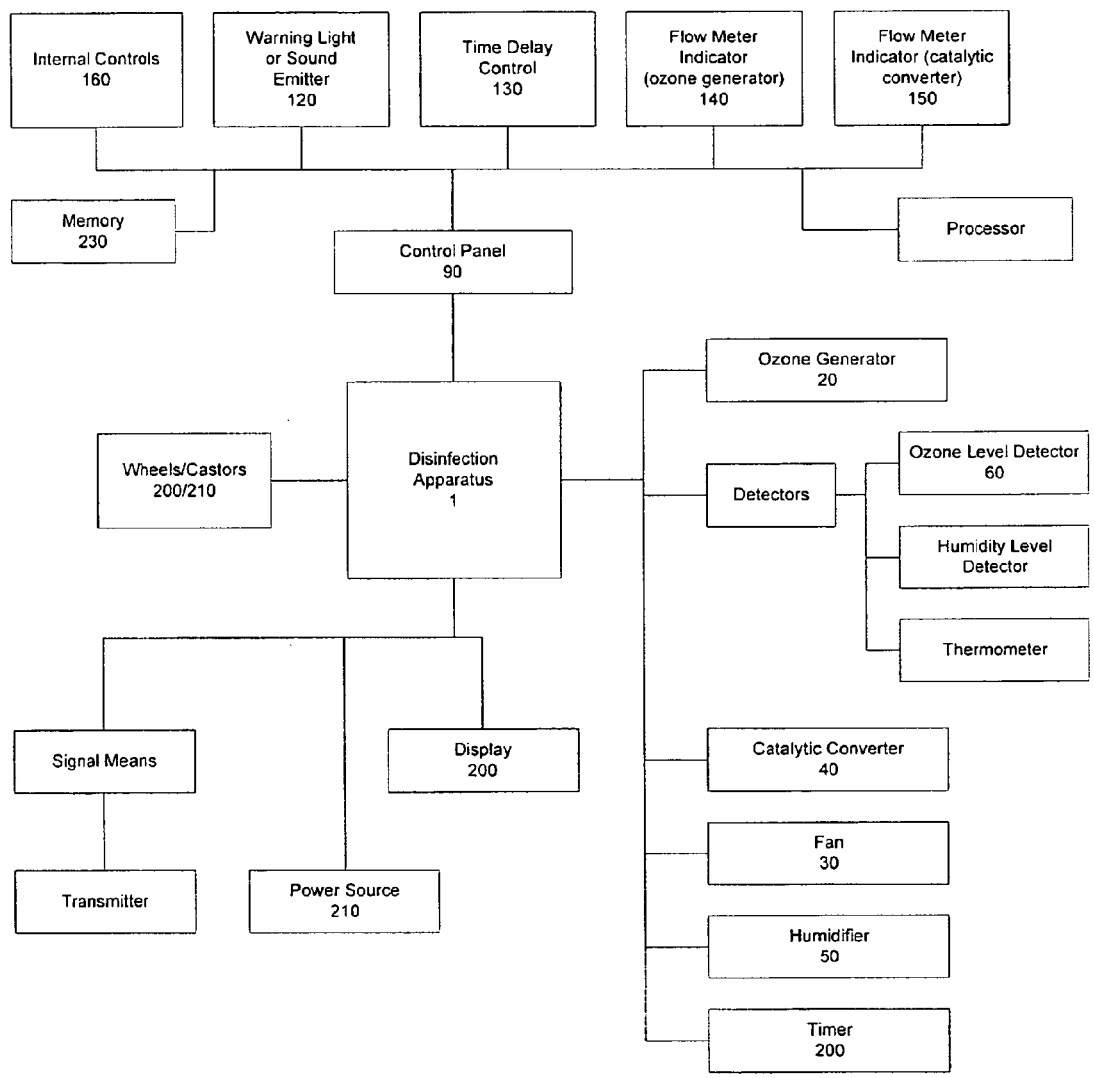
FIG. 4 is a block diagram thereof.

The disinfection apparatus also preferably has the following components (as seen in FIG. 4):
1. a timer 200 to record the number of hours or minutes disinfection apparatus 1 has been operating and to turn on or off ozone generator 20 when the appropriate time has passed;
2. a warning light or sound emitter 120 to indicate that the disinfection apparatus is generating ozone or that the ozone level is unsafe;
3. a time delay control 130 to allow for a delay before disinfection apparatus 1 begins to generate ozone, allowing the user to exit the closed environment;
4. one or more other time delay switches for the operation of the catalytic converter, humidifier, and other features;
5. a ozone flow meter 140 to indicate the air flow moving through the ozone generator 20;
6. a catalytic converter flow meter 150 to indicate the airflow moving through the catalytic converter 40;
7. a control panel 90 to operate disinfection apparatus 1, and display which operations of the disinfection apparatus are working either individually or with others;
8. further alarms included in the instrumentation that would indicate a malfunction of the disinfection apparatus;
9. an internal control 160 to allow for variance of the ozone concentration to be achieved;
10. sliding inspection panels to allow for easy maintenance and inspection of the apparatus;
11. separate electric fittings and plugs to allow for ancillary apparatus such as an additional ozone scrubber to be connected to the apparatus;
12. a memory 230 to record timing required in previous disinfection processes (e.g. the time taken to reach the desired ozone and humidity levels).

Disinfection apparatus 1 also has power source 210 which can be a cord and plug for insertion into a suitable outlet, or batteries. Disinfection apparatus 1 also has displays 200 preferably showing the current ozone concentration, humidity and temperature.

Figure 7:
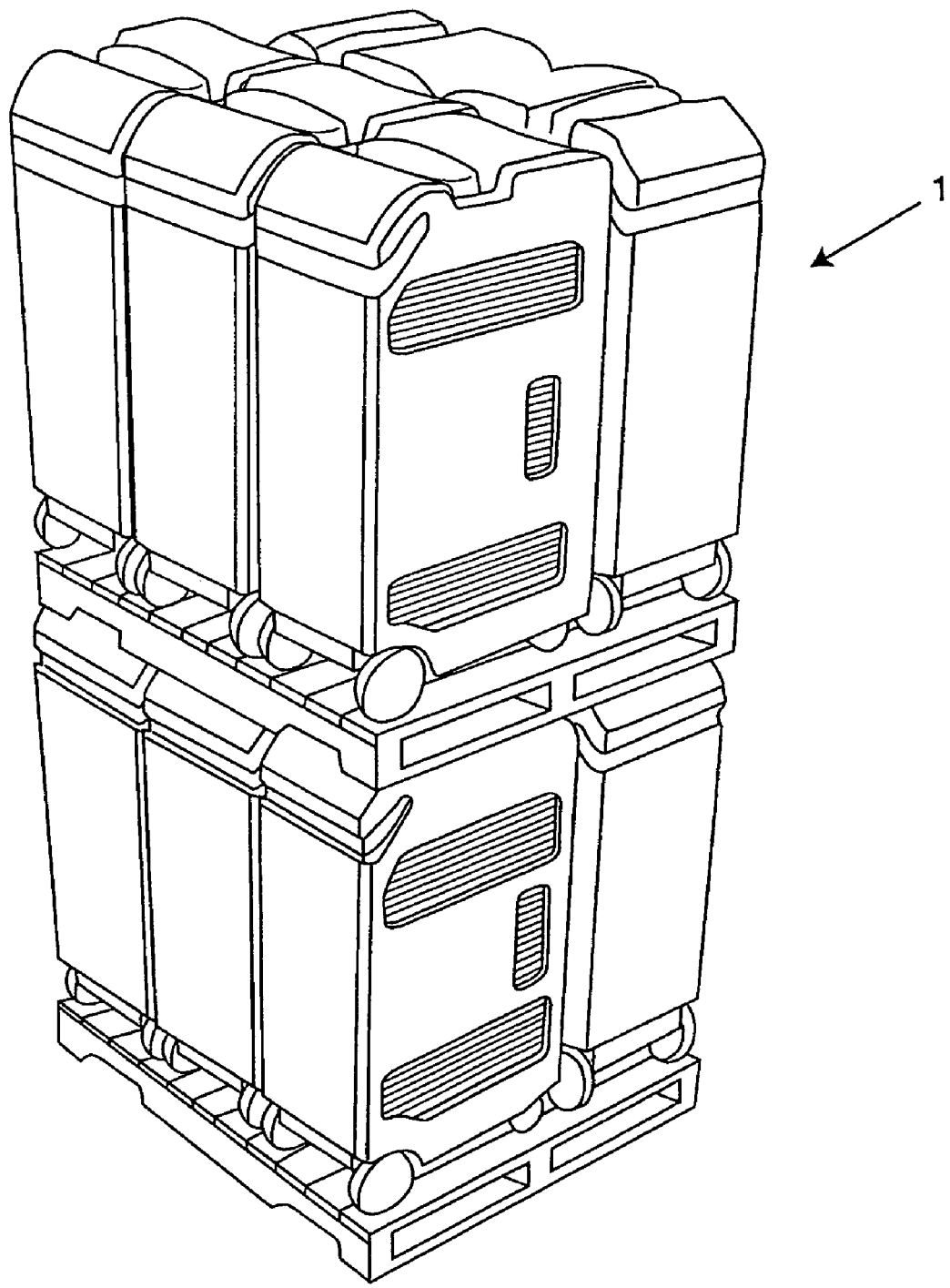
FIG. 7 is a perspective view of a plurality of disinfection apparatuses according to the invention stacked on a pallet.

In a preferred embodiment as shown in FIG. 7, disinfection apparatus 1 is stackable and sized to fit on a standard pallet. This allows disinfection apparatus 1 to be easily stored on cruise ships and the like when not in use.

USE EXAMPLE 1

Hotels

The hotel industry is based on frequent visitors to particular rooms, and such visitors often only stay a single night. Hotels are also one of the worst effected by disease scares such as SARS, as tourism is one the industries most keenly effected. Hotels have also been using ozone at low concentrations to reduce odours in rooms.

As used in hotels according to the method, a maid after initially cleaning a vacated room (preferably after the guest had checked out) would place the disinfection apparatus in the room, set it for the specified ozone concentration, and leave the room (including locking the door), returning when the time had passed and the ozone concentration was reduced to safe levels. The disinfection apparatus can then be taken to the next appropriate room.

At the end of the process, the ozone would kill the viruses, bacteria and fungi left by the departing person(s). A dormitory could go through a similar disinfection process.

USE EXAMPLE 2

Airplanes

The airline industry is another industry prone to financial losses when fear of a disease outbreak strikes. To use the method according to the invention on an airliner, after the airliner is initially cleaned, one or more disinfection apparatuses are used within the airliner. During the period of high ozone levels, access to the interior of the airplane should be prevented.

Once the necessary time has passed, and the ozone concentrations are safe, the interior of the airplane is accessed and the disinfection apparatuses can be removed.

USE EXAMPLE 3

Cruise Ships

Cruise ships present an environment where a disease can spread rapidly due to the confinement of a large number of people in a relatively small environment. The method according to the invention is useful when the ship is docked and few people are about, in which case the method is used in a manner very similar to that of the hotel example described previously. Alternatively, the disinfection apparatus could be used within a cabin when the inhabitants report certain symptoms. The disinfection apparatus could also be used in both public areas (which may require more than one disinfection apparatus), and smaller high traffic areas (such as gift shops).

USE EXAMPLE 4

Hospitals

A yet further example of a location in which the method according to the invention is useful is a hospital. Obviously hospitals are areas in which viruses, bacteria and other disease causing agents are common, as those diseased often end up in such a location. When a hospital room is vacated, perhaps even only temporarily, the method according to the invention could be carried out to kill any viruses or bacteria left by the last patient staying in such room. It may also be beneficial to use the disinfection apparatus in emergency areas, operating theatres, and the like when such area is exposed to a particularly problematic disease (such as SARS).

Effectiveness of Gaseous Ozone

Generally tests were conducted to show that ozone gas can efficiently inactivate (kill) selected viruses tested, such as, herpes simplex virus, influenza virus, corona virus, poliovirus and rhinovirus. These viruses were found to be vulnerable to ozone in a gaseous state on surfaces such as glass, plastic, steel, wood and fabric. Increasing the concentration of ozone and greater times of exposure were more effective, as anticipated, and rapidly increasing the relative humidity after reaching the desired ozone concentration also significantly increased the antiviral efficacy.

Experiment #1

Ozone was generated within a chamber to provide an ozone concentration of approximately 100 ppm for 30 minutes on a variety of surfaces, including glass slides, steel disks, etc. Relative humidity and temperature were recorded.

Herpes Simplex Virus ("HSV"), Feline calicivirus ("FCV"), and murine coronavirus ("MCV") were all dramatically inactivated by exposure to ozone gas. Typically a dosage of 100 ppm for 20-30 minutes reduced the virus by more than 99%. Shorter exposure times resulted in significant though smaller reductions. Thus 10 minutes of exposure inactivated approximately 90-95% virus infectivity, whereas shorter time periods were less effective. It appeared, from a number of the time course studies made, that a period of between 5 and 10 minutes exposure to ozone was required to absorb the gas and effect the appropriate chemical processes, before loss of infectivity occurred. Poliovirus was also inactivated by ozone under similar conditions.

Exposure of the viruses to ozone was made on samples dried on six different surfaces, relevant to materials encountered in the hospitality industry, namely glass, plastic, stainless steel, wood, fabric, and carpet. Several viruses were evaluated on each surface. In general, the viruses were susceptible to ozone on glass, plastic, steel, wood, and fabric.

The results of numerous time course experiments, with different virus-surface combinations, confirmed that increasing time of exposure resulted in greater inactivation of virus, and in some cases no virus infectivity could be detected at all after 30 minutes exposure.

In several experiments the effect of relative humidity was examined by incorporating a container of warm water into the chamber during exposure. It was difficult to control exact humidity levels in this manner; nevertheless it was clear that in high humidity virus was inactivated by ozone much more efficiently than in ambient humidity (which was usually 45-50%).

Experiment #2

A further experiment was conducted to test the effect of ozone gas against selected viruses, under conditions similar to those in a hotel room. The aim was to measure the amount of ozone inactivation of HSV in several different locations within a test room and to compare the efficacy of ozone inactivation of three different viruses (HSV, poliovirus and rhinovirus) placed within the test room.

The three samples of HSV were inactivated (killed) by 98%, 99.4% and 97.8%. The ozone concentration was 28 ppm and the time of exposure was 60 minutes (it also took 30 minutes to reach that ozone concentration from a starting point of 0).

As the inactivation was similar at three different locations within the room, this indicates that the ozone gas is very effective at inactivating viruses within a large room.

Experiment #3

A further experiment was conducted to evaluate the effect of ozone gas against FCV, the surrogate virus for Norwalk virus, in comparison with HSV and poliovirus, under conditions of reduced ozone doses and high humidity.

The FCV was inactivated by 99.91%; the poliovirus was inactivated by much more than 99.6%; and the HSV was inactivated by much more than 99%. The closed interior environment used for these tests was provided an atmosphere of high humidity, and with substantially reduced ozone dosage (between 20 ppm and 40 ppm) for about 15 minutes. It was concluded that FCV can be inactivated more than 99.9% by exposure to ozone gas in the presence of high relative humidity and it should be possible to inactivate this virus (and by extrapolation Norwalk virus) even further by optimizing the ozone dosage and humidity.

Experiment #4

A further experiment was conducted to develop an appropriate and relevant experimental system for testing the efficacy of quantified ozone doses in inactivating (i.e. killing) known amounts of several important human viruses; to derive viricidal killing curves for known doses of ozone gas against samples of dried viruses on several different surfaces relevant to the hospitality industry; to compare the viricidal efficacy of ozone gas against five selected viruses known to be important in human health; to examine the effects of different parameters on the viricidal efficacy of ozone gas, including: concentration of ozone, time of exposure, and relative humidity; and to consider the potential for additional applications of ozone gas as a sterilizing agent in other situations where viral and microbial agents could pose threats.

The experiments showed that ozone gas can efficiently inactivate (kill) all of the five selected viruses tested, namely, herpes simplex virus, influenza virus, corona virus, rhinovirus, and poliovirus. These viruses are vulnerable to ozone gas in the dried state on different surfaces, such as glass, plastic, steel, wood and fabric. Increasing doses of ozone and greater times of exposure were more effective, as anticipated, and increasing relative humidity also significantly increased the antiviral efficacy.

Based on these results, the viruses tested are efficiently inactivated by gaseous ozone, on each of the surfaces tested, under conditions relevant to practical applications. Therefore ozone gas also has potential as a safe antiviral and antimicrobial agent in various other situations that are accessible to a small, portable, ozone generating machine.

HSV, FV, and MCV were all dramatically inactivated by exposure to ozone gas. Typically a dosage of 100 ppm for 20 to 30 minutes reduced the virus by more than 99%. Shorter exposure times resulted in significant though smaller reductions. Thus 10 minutes inactivated approximately 90-95% of the virus infectivity, whereas shorter time periods were less effective. It appeared, from a number of the time course studies made, that a period of between 5 and 10 minutes exposure to ozone was required to absorb the gas and effect the appropriate chemical processes, before loss of infectivity occurred. Presumably oxidation of particular viral components is required, and that this process requires several minutes. Following this process, inactivation, i.e. loss of infectivity, is rapid.

Exposure of the viruses to ozone was made on samples dried on six different surfaces, relevant to materials encountered in the hospitality industry, glass, plastic, stainless steel, wood, fabric, and carpet. Several viruses were evaluated on each surface. In general, the viruses were susceptible to ozone on such surfaces.

In several experiments the effect of relative humidity was examined by incorporating a container of warm water into the chamber during exposure. It was difficult to control exact humidity levels in this manner; nevertheless it was clear that in high humidity the virus was inactivated by ozone much more efficiently than in ambient humidity (which was usually 45-50%).

Experiment #5

Further experiments were conducted to determine the inactivation of the Norwalk virus and to do research regarding an ozone scrubber. It had already been demonstrated that several viruses, including the feline calicivirus (the recommended surrogate virus for testing Norwalk virus susceptibility to anti-viral agents), could be inactivated by ozone gas.

The objective of the experiment was to optimize the ozonation protocols in order to minimize the effective dose and exposure times required, to determine the degree of relative humidity preferred, and to confirm the optimal protocols for virus specimens resembling field conditions (i.e. in different biological fluids and on "unclean surfaces").

The feline calicivirus is used in these test procedures because Norwalk virus itself is difficult to grow and measure in cell cultures. However, once optimal conditions for ozone inactivation of calicivirus have been determined, then reference stool specimens known to contain Norwalk virus can be tested.

The data confirmed that FCV, and therefore Norwalk virus, can be efficiently inactivated by our disinfection apparatus under standard conditions and at durations, temperature and humidity levels which would be appropriate for the cruise liner and hotel industries.

Experiment # 6—Cruise Ship Tests

Samples of FCV were placed in a cruise ship cabin of approximately 1300 square feet. The ozone level in the cabin was raised to 20.3 ppm, which took 15 minutes. After this, the humidity in the cabin was raised to 98% (which took four minutes). The catalytic converter was then turned on for 20 minutes. This resulted in over 98.8% inactivation of the FCV samples.

Experiment #7—Hotel Room Test

Samples of FCV and influenza virus were placed in a hotel room. The ozone level of the hotel room was raised to 25 ppm, after which the humidity level was rapidly raised to 92%. Both the ozone generator and humidifier were then turned off and the room "soaked" for 15 minutes. Then the catalytic converter was used for 20 minutes to bring the ozone level down to 1 ppm. This resulted in over 98% inactivation of the FCV and influenza virus samples.

Diseases Effected

Other disease causing agents such as viruses and bacteria that ozone is effective against include: *Clostridium difficile* (a human pathogenic bacterium of the gut); Antibiotic-Resistant bacteria (*E. coli, Staphylococcus* and *Streptococcus*, including the multiple antibiotic-resistant strain (MRSA) of Staph); *Candida albicans* (a yeast); and fungi growing on different surfaces. A wide range of micro-organisms, including Gram-positive and Gram-negative bacteria, as well as yeasts and molds, are also inactivated by ozone gas. Bacteria successfully demonstrated to be susceptible include: *Bacillus* sp; *Clostridium difficile*, spores and cells; *E. coli* (*Escherichia coli*); *Klebsiella pneumoniae; Legionella pneumophila; Propionibacterium acnes; Pseudomonas aeruginosa; Staphylococcus aureus*; methicillin-resistant (MRSA) and -sensitive (MSSA);); *Stereptococcus pyogenes; Acinetobacter baumanii*; vancomycin resistant, *Enterobacter; Hemophilus influenzae*; and *Mycobacterium smegmatus*.

Bacteria expected to be susceptible includes species of the following genera: *Campylobacter*; other *Clostridium* sp (perfringens, botulinum, sporogenes); *Enterococcus; Helicobacter; Lactobacillus; Listeria; Neisseria; Proteus; Salmonella; Shigella; Vibrio*; and *Yersinia*.

Fungi demonstrated by laboratory tests to be susceptible include: *Aspergillus* sp.; *Candida albicans; Penicilium* sp.; *Stachybotris chartarum; Trichoderma* sp.; *Ulocladium* sp.; *Alternaria* sp.; *Botrytis* sp.; *Cladosporium* sp.; *Geotrichum* sp.; and *Mucor* sp.

Fungi anticipated to be susceptible, include *Cryptococcus* sp.

Other organisms anticipated to be susceptible include: Bed Bugs (Cimex lectularius); and House Dust Mites (*Dermatophagoides farinae* in North America), which is one of the most common causes of asthma.

Although the particular preferred embodiments of the invention have been disclosed in detail for illustrative purposes, it will be recognized that variations or modifications of the disclosed apparatus lie within the scope of the present invention.

The invention claimed is:

1. A method of sanitizing or disinfecting a closed environment comprising:
    (a) generating gaseous ozone into said closed environment to a predetermined ozone concentration of at least 20 ppm;
    (b) after reaching said predetermined ozone concentration, using a humidifier to rapidly increase the humidity of said closed environment to a predetermined relative humidity level of greater than 80%, wherein said relative humidity level is reached and the humidifier is inactivated in four to eight minutes;
    (c) after reaching said predetermined relative humidity level, depleting said ozone; and
    (d) when said ozone concentration is reduced to a predetermined safe level, signalling.

2. The method of claim 1, wherein said closed environment is used for human habitation.

3. The method of claim 2, wherein the closed environment is a room or a cabin.

4. The method of claim 1, wherein said relative humidity level is 90% or more.

5. The method of claim 4, wherein said relative humidity level is about 98%.

6. The method of claim 1, wherein said predetermined ozone concentration is between 20 and 30 ppm.

7. The method of claim 1, wherein the gaseous ozone is generated using a corona discharge apparatus.

8. The method of claim 1, wherein the ozone is depleted to about 0.10 ppm or less.

9. The method of claim 8, wherein said depleting of ozone occurs within about fifteen minutes.

10. The method of claim 1, wherein the ozone is depleted using a catalytic converter.

11. The method of claim 10, wherein the catalytic converter passes ozonated air through a manganese dioxide tray.

12. The method of claim 10, wherein the catalytic converter passes ozonated air through an activated carbon tray.

13. The method of claim 1, wherein the humidity level is raised by an ultrasonic humidifier.

14. The method of claim 1, wherein said signalling is turning on an LED.

15. The method of claim 1, wherein said signalling is turning off a sound.

16. The method of claim 1, wherein ozone generation ceases at about the commencement of step (b).

17. The method of claim 1, wherein ozone generation ceases at about the same time as inactivation of the humidifier.

18. The method of claim 1, wherein the ozone is depleted to said predetermined safe level within 15 minutes.

* * * * *